United States Patent [19]

Kondo et al.

[11] Patent Number: 4,536,220
[45] Date of Patent: Aug. 20, 1985

[54] FLUORAN DERIVATIVES AS NEW COMPOUNDS AND RECORDING SYSTEM UTILIZING THE SAME AS COLORLESS CHROMOGENIC MATERIAL

[75] Inventors: Mitsuru Kondo, Hyogo; Hiroshi Iwasaki, Kawanishi; Haruo Omura, Motomachi; Nobuo Kanda, Osaka, all of Japan

[73] Assignee: Kanzaki Paper Manufacturing Co., Ltd., Tokyo, Japan

[21] Appl. No.: 562,738

[22] Filed: Dec. 19, 1983

[30] Foreign Application Priority Data

Dec. 27, 1982 [JP] Japan ................................ 57-233077
Jan. 20, 1983 [JP] Japan .................................. 58-8544
Aug. 10, 1983 [JP] Japan ................................ 58-147057

[51] Int. Cl.³ ............................................. C09D 11/00
[52] U.S. Cl. ...................................... 106/21; 346/221; 427/151; 549/225; 549/226
[58] Field of Search ......................... 106/21; 282/27.5; 427/151; 549/225, 226; 346/221

[56] References Cited

U.S. PATENT DOCUMENTS 3,959,571  5/1976  Yahagi et al. ...................... 428/537

Primary Examiner—Paul Lieberman
Assistant Examiner—Amelia B. Yarbrough
Attorney, Agent, or Firm—Fisher, Christen & Sabol

[57] ABSTRACT

A new fluoran derivative useful as a colorless chromogenic material has the following formula:

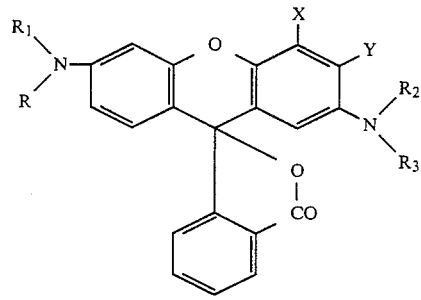

wherein $R$, $R_1$, $R_2$, $R_3$, $X$ and $Y$ have the same meaning as defined hereinbefore.

8 Claims, No Drawings

FLUORAN DERIVATIVES AS NEW COMPOUNDS AND RECORDING SYSTEM UTILIZING THE SAME AS COLORLESS CHROMOGENIC MATERIAL

BACKGROUND OF THE INVENTION

This invention relates to fluoran derivatives as new compounds useful as colorless chromogenic materials and a new recording system utilizing the same.

There are known various kinds of recording systems utilizing the colorforming reaction between a colorless chromogenic material and an electron accepting acidic reactant material by the medium of mechanical, heat, electric or light energy. Among them there are included a pressure-sensitive record sheet, a heat-sensitive record sheet, an electrothermal record sheet, an ultrasonic record sheet, an electron beam record sheet, an electrostatic record sheet and a photosensitive record sheet. The colorless chromogenic materials of these kinds also find their usefulness in photosensitive printing compositions, typewriter ribbons, ball-point pen ink, crayon and stamp ink.

In the recording system utilizing the color forming reaction between a colorless chromogenic material (hereinafter referred to as "color former") and an electron accepting acidic reactant material (hereinafter referred to as "acceptor"), images of various colors can be developed by using different kinds of color formers. There is now an increased demand for record materials which develop black color images which can be reproducible for copies. Theoretically, images of substantially black color can be obtained by using a mixture of various color formers which develop the respective different colors, e.g., red, blue, yellow and green. The utilization of a mixture of different color formers for obtaining a black color has, however, a disadvantage that the once developed black color images cannot be maintained for a long time because different color formers have different color developing speeds and different light and moisture resistances. Some attempts have been made to obtain images of substantially black color through the utilization of a single color former. However, there has yet been found no single color former which can develop substantially black color images without sacrificing all the stability of the color former before color developing, color developing speed, color density, color tone and stability of the color images developed and its production cost.

The primary object of the invention is to provide novel fluoran derivatives useful as color formers for use in various recording systems.

Another object of the invention is to provide novel color formers for use in recording systems in which the color images when developed therefrom assume a substantially deep-black color and have a good light resistance.

A further object of the invention is to provide novel color formers for use in heat sensitive recording systems in which substantially no fogging occurs on the record materials to which they are applied.

A still further object of the invention is to provide novel color formers for use in recording systems which have a good and instant color developability.

It is also included among the objects of the invention to provide an improved recording system in which a fluoran derivative as a new compound is used as a color former and the color images when developed therefrom have a good light resistance and assume a substantially deep-black color which is suitable for reproduction of copies.

Other objects and advantages of the invention will become apparent from the following description.

SUMMARY OF THE INVENTION

The novel fluoran derivatives according to the invention have the following formula:

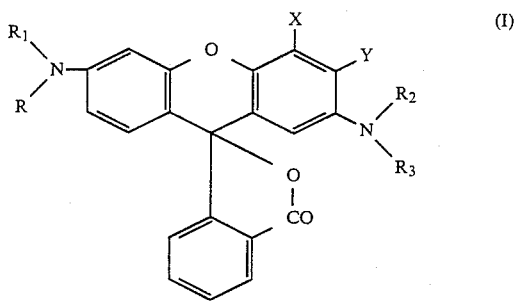

wherein R is cyclopentyl, cycloheptyl, cyclohexylmethyl or cyclohexyl substituted by at least one alkyl and having 7 to 10 carbon atoms; each $R_1$, $R_2$ and $R_3$ is hydrogen, an alkyl having 1 to 18 carbon atoms which may be substituted by at least one substituent selected from the group consisting of halogen atoms, alkoxyls and cyano, or an aralkyl which may be substituted by at least one substituent selected from the group consisting of halogen atoms, lower alkyls and lower alkoxyls, or both of $R_2$ and $R_3$ together with the adjacent nitrogen may form a heterocyclic ring which may include an oxygen or another nitrogen, or $R_3$ is a cycloalkyl or aryl which may be substituted by at least one substituent selected from the group consisting of halogen atoms, lower alkyls, substituted alkyls, lower alkoxyls, amino, substituted aminos and acyls; each X and Y is hydrogen, a halogen atom or a lower alkyl or Y is a lower alkoxyl.

The fluoran derivatives having the above formula (I) can be used as color formers for use in various recording systems including a pressure-sensitive recording system and a heat-sensitive recording system. The compounds according to the invention can produce a deep color upon contact with an acceptor. The color images produced have a good light resistance and can stably maintain their color tone initially produced.

Particularly, the fluoran derivatives having the following formula:

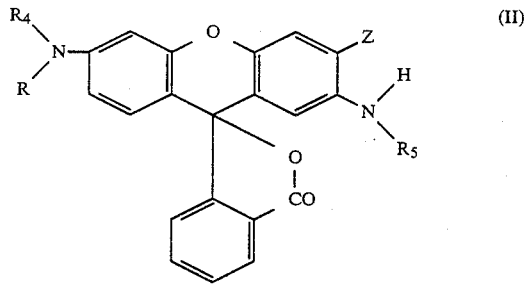

wherein R is the same as above defined, $R_4$ is an alkyl having 1 to 18, preferably 1 to 8, carbon atoms, $R_5$ is a phenyl which may be substituted by at least one substituent selected from the group consisting of low alkyls, halogen atoms and dialkylaminos, and Z is a lower alkyl, are preferable compounds which can produce a deep black, reddish black or greenish black color upon contact with acceptors. The color images produced with the use of those compounds can maintain their clear color tone for a long time. The pressure-sensitive record materials utilizing those compounds show an instant color developability. The heat-sensitive record materials utilizing those compounds have a good color developability while substantially no fogging is caused thereon.

Each of the lower alkyl and lower alkoxyl described above may preferably have 1 to 5 carbon atoms.

DETAILED DESCRIPTION OF THE INVENTION

The compounds represented by the formula (I) may preferably be prepared by reacting 2-(2-hydroxy-4-substituted amino)benzoylbenzoic acid derivatives represented by the following formula:

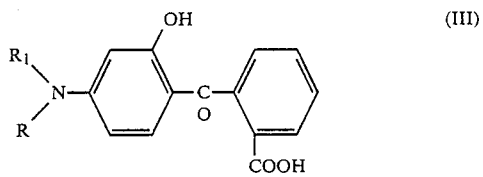

wherein R and $R_1$ are the same as above defined, respectively, with p-aminophenol derivatives represented by the following formula:

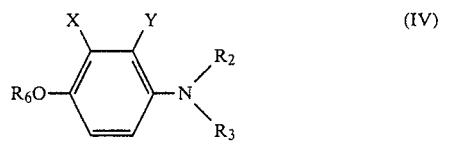

wherein $R_2$, $R_3$, X and Y are the same as above defined, respectively, and $R_6$ is hydrogen or a lower alkyl, in the presence of a condensing agent.

The compounds represented by the formula (III) may preferably be prepared by making m-substituted aminophenol derivatives represented by the formula (V) react with phthalic anhydride represented by the formula (VI) as follows:

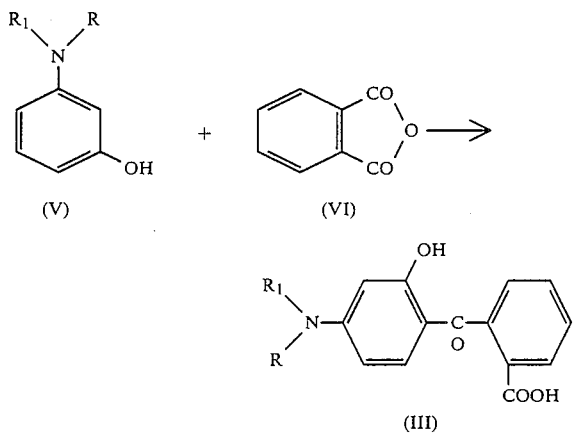

wherein R and $R_1$ are the same as above defined.

The condensing agent used for the reaction between the compound represented by the formula (III) and the compound represented by the formula (IV) may preferably be at least one Friedel-Crafts Type Catalyst such as sulfuric acid; phosphorus pentoxide; phosphoric acid; polyphosphoric acid; anhydrous metal halide such as anhydrous tin chloride, anhydrous zinc chloride, anhydrous aluminum chloride, anhydrous tin bromide, anhydrous zinc bromide, anhydrous aluminum bromide and anhydrous iron bromide; phosphorus trichloride; phosphorus tribromide; phosphorus pentachloride; phosphorus pentabromide; anhydrous boron trifluoride; and hydrofluoric acid. The most preferred condensing agent is sulfuric acid.

Among useful solvents in the above reaction, there are included carbon disulfide, monochlorobenzene, dichlorobenzene, trichlorobenzene, nitrobenzene, nitromethane and nitroethane. Sulfuric acid which is the most preferred condensing agent also functions as a good solvent.

In the reaction of the compound represented by the formula (III) with the compound represented by the formula (IV) in the presence of the above-mentioned condensing agent, if $R_6$ is a lower alkyl in the compound represented by the formula (IV), there are occasionally produced triphenylmethane derivative represented by the following formula:

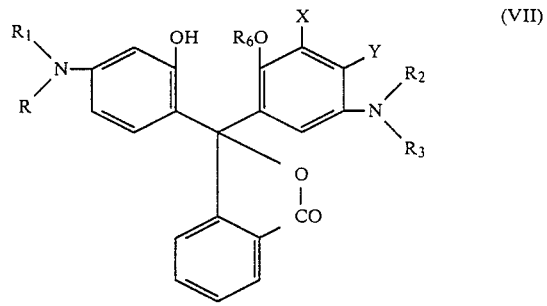

wherein R, $R_1$, $R_2$, $R_3$, $R_6$, X and Y are the same as above defined, respectively.

The above triphenylmethane derivatives represented by the formula (VII) can be changed to the compounds represented by the formula (I) by taking the following steps:

preparing an aqueous system including the derivatives represented by the formula (VII);

adjusting the pH of the aqueous system to higher than 9.0, by addition of basic materials such as NaOH, KOH and the like; and then heating the aqueous system to a temperature of 50° C. to 100° C.

In order to increase the yield of the compounds represented by the formula (I) in above manner an organic solvent such as acetone, benzene, toluene or xylene may preferably be added to the aqueous system including the triphenylmethane derivatives represented by the formula (VII). Hydrophobic organic solvents such as benzene, toluene and xylene are especially advantageous to effectively prevent by-products from being formed.

The fluoran derivatives thus obtained according to the invention are substantially colorless chromogenic compounds which can develop a deep color of substantially black upon contact with acceptors. The above mentioned fluoran derivatives may be used either solely or in combination.

The acceptors used are selected according to the kinds of record materials. The materials which are preferably used as acceptors for pressure-sensitive record materials, heat-sensitive record materials, and electrothermal record materials are those which function as Bronsted or Lewis acid. Among them there are included: inorganic acceptors such as acid clay, activated clay, attapulgite, bentonite, colloidal silica, aluminum silicate, magnesium silicate, zinc silicate, tin silicate, calcined kaolin and talc; organic acceptors such as aliphatic carboxylic acids, e.g., oxalic acid, maleic acid, tartaric acid, citric acid, succinic acid and stearic acid, aromatic carboxylic acid, e.g., benzoic acid, p-tert-butylbenzoic acid, phthalic acid, gallic acid, salicylic acid, 3-isopropylsalicylic acid, 3-phenylsalicylic acid, 3-cyclohexylsalicylic acid, 3,5-di-tert-butylsalicylic acid, 3-methyl-5-benzylsalicyclic acid, 3-phenyl-5-($\alpha,\alpha$-dimethylbenzyl)salicyclic acid, 3,5-di-($\alpha$-methylbenzyl)salicylic acid and 2-hydroxy-1-benzyl-3-naphthoic acid, phenolic compounds, e.g., 4,4'-isopropylidenediphenol, 4,4'-isopropylidenebis(2-chlorophenol), 4,4'-isopropylidenebis(2,6-dibromophenol), 4,4'-isopropylidenebis(2,6-dichlorophenol), 4,4'-isopropylidenebis(2-methylphenol), 4,4'-isopropylidenebis-(2,6-dimethylphenol), 4,4'-isopropylidenebis(2-tert-butylphenol), 4,4'-sec-butylidenebisphenol, 4,4'-cyclohexylidenebisphenol, 4,4'-cyclohexylidenebis(2-methylphenol), 4-tert-butylphenol, 4-phenylphenol, 4-hydroxydiphenoxide, $\alpha$-naphthol, $\beta$-naphthol, dimethyl-4-hydroxyphthalate, benzyl-4-hydroxybenzoate, 2,2'-thiobis-(4,6-dichlorophenol), 4-tert-octylcatechol, 2,2'-methylenebis(4-chlorophenol), 2,2'-methylenebis(4-methyl-6-tert-butylphenol) and 2,2'-dihydroxydiphenyl, phenol resins, e.g., p-phenylphenolformaldehyde resin and p-butylphenol-acetylene resin; salts of the above organic acceptors with polyvalent metals such as zinc, magnesium, aluminium, calcium, titanium, manganese, tin and nickel; and inorganic acid such as hydrogen halide, e.g., hydrogen chloride, hydrogen bromide and hydrogen iodide, boric acid, silicic acid, phosphoric acid, sulfuric acid, nitric acid, perchloric acid and halides of aluminium, zinc, nickel, tin, titanium, boron and the like.

Some embodiments of the utilization of the fluoran derivatives according to the invention for various kinds of record materials are described hereinbelow:

The fluoran derivatives can be utilized for various kinds of pressure-sensitive record materials, e.g., those disclosed in U.S. Pat. Nos. 2,505,470, 2,505,471, 2,505,489, 2,548,366, 2,712,507, 2,730,456, 2,730,457, 3,418,250, 3,924,027 and 4,010,038.

A typical method for the production of a pressure-sensitive record material utilizing the fluoran derivatives according to the invention is as follows:

At least one of the fluoran derivatives according to the invention is dissolved in a solvent to form a solution which may include synthetic oil such as alkylated naphthalene, alkylated diphenyl, alkylated diphenylmethane and alkylated terphenyl, vegetable oil such as cotton seed oil and castor oil, animal oil and mineral oil or mixtures of the foregoing. The solution may additionally include basic colorless chromogenic material such as triphenylmethane lactones, spiropyrans, fluorans, diphenyl-methanes and Leucomethylene Blue. The solution of the fluoran derivative may be dispersed in a binder to form a coating composition. The solution may be enclosed in microcapsules through the utilization of the coacervation technique, the interfacial polymerization technique, the in-situ polymerization technique or any other method for making oil droplet-containing microcapsules and the microcapsules thus prepared are dispersed in a binder to form a coating composition. Any one of the coating compositions thus prepared is applied to a base sheet such as a paper sheet, plastic sheet, resin coated paper sheet, etc. to obtain a pressure-sensitive record material. In case where the pressure-sensitive copying system consists of a top sheet, a bottom sheet and, if necessary, at least one middle sheet, the pressure-sensitive record material according to the invention is used as the top sheet and the middle sheet. The pressure-sensitive record material according to the invention also be utilized in the "self contained" system in which both the colorless chromogenic material and the acceptor are dispersed on one surface of the same sheet. The pressure-sensitive record material utilizing the fluoran derivative according to the invention can produce clear color images having a good light resistance.

The fluoran derivatives according to the invention are also useful for production of various kinds of heat-sensitive record materials, e.g., as disclosed in Japanese Patent Publications Nos. 3,680 of 1969, 27,880 of 1969, 14,039 of 1970, 43,830 of 1973, 69 of 1974, 70 of 1974 and 20,142 of 1977. Most typically, heat-sensitive record materials may be produced by coating a coating composition including a binder, fine particles of the fluoran derivative according to the invention and the acceptor on a base sheet such as paper sheet, plastic film, synthetic paper sheet, woven fabric sheet or mold. The amount of the acceptor in the recording layer may be within the range of 1 to 50 parts by weight, preferably within the range of 2 to 10 parts by weight, per one part by weight of the chromogenic material used. The coating composition may include inorganic metal compounds such as oxides, hydroxides and carbonates of polyvalent metals and/or inorganic pigments in an amount of 0.1 to 5 parts by weight, preferably, 0.2 to 2 parts by weight, per one part by weight of the amount of the acceptor. The recording layer may also include dispersing agents, ultraviolet ray absorbing agents, heat fusible materials, antifoaming agent, fluorescent dye, coloring dyes and other adding materials.

The fluoran derivative and the acceptor may be applied to a base sheet either in the form of a single coating composition or in the form of two separate coating compositions which may be applied one-by-one. Application of the fluoran derivative and acceptor to a base sheet may also be carried out by impregnation or by sizing. The amount of the coating composition including the fluoran derivative and the acceptor may preferably be within the range of 2 to 12 g/cm$^2$. Among the useful binder materials there may be included starches, celluloses, proteins, gum arabic, polyvinyl alcohol, salts of styrene-maleic anhydride copolymer, sytrene-butadiene copolymer emulsions, salts of vinyl acetate-maleic anhydride copolymer and salts of polyacrylic acid.

The electrothermal record materials may be produced according to any known methods such as those disclosed in Japanese Laid-Open Patent Publications Nos. 11,344 of 1974 and 48,930 of 1975. Usually, the record material of this type may be produced, either by coating on a base sheet, such as a paper sheet, a coating composition consisting of a dispersion of an electroconductive material, a basic dye material essentially comprising the fluoran derivative according to the invention, an acceptor and a binder, or by coating an electroconductive material on a basic sheet to form an electroconductive layer thereon and further coating on the electroconductive layer another coating composition consisting of a dispersion of the fluoran derivative according to the invention, an acceptor and a binder. In case where each of the fluoran derivative and the acceptor used is not fusible within the temperature range of 70° to 120° C., an appropriate heat fusible material may be added for controlling the heat sensitivity.

PREFERRED EMBODIMENTS OF THE INVENTION

The following examples serve to illustrate the invention in more detail although the invention is not limited to the examples. Unless otherwise indicated, parts and % signify parts by weight and % by weight, respectively.

EXAMPLE 1

0.011 mol of 2-(2-hydroxy-4-N-ethyl-N-cyclopentylamino)benzoylbenzoic acid was reacted with 0.010 mol of 2-methyl-4-methoxyldiphenylamine in 15 ml of concentrated sulfuric acid at room temperature for 24 hours. The reaction product was poured into 100 ml of ice-cold water. The aqueous system was adjusted to pH11 with 20% aqueous solution of sodium hydroxide at room temperature and then mixed with 50 ml of toluene. The mixture was heated at 85° C. for 3 hours. The toluene layer was separated and toluene was distilled away under reduced pressure to obtain a solid. The solid was recrystallized from ethylalcohol to obtain 3-N-ethyl-N-cyclopentylamino-6-methyl-7-anilinofluoran as a needles in a 83% yield. The fluoran derivative has a melting point of 169°–170° C. and became black upon contact with silica gel.

EXAMPLE 2

Example 1 was repeated except that 2-(2-hydroxy-4-N-ethyl-N-cyclohexylmethylamino)benzoylbenzoic acid was used instead of 2-(2-hydroxy-4-N-ethyl-N-cyclopentylamino)benzoylbenzoic acid to obtain 3-N-ethyl-N-cyclohexylmethylamino-6-methyl-7-anilinofluoran as a needles in a 85% yield. The fluoran derivative has a melting point of 165°–169° C. and became black upon contact with silica gel.

EXAMPLE 3

Example 1 was repeated except that 2-(2-hydroxy-4-N-ethyl-N-3',3',5'-trimethylcyclohexylamino)benzoylbenzoic acid was used instead of 2-(2-hydroxy-4-N-ethyl-N-cyclopentylamino)benzoylbenzoic acid to obtain 3-N-ethyl-N-3',3',5'-trimethylcyclohexylamino-6-methyl-7-anilinofluoran as a colorless needles in a 83% yield. The fluoran derivative has a melting point of 154°–156° C. and became black upon contact with silica gel.

EXAMPLE 4

0.01 mol of 2-(2-hydroxy-4-N-methyl-N-cyclopentylamino)-benzoylbenzoic acid was reacted with 0.01 mol of 2-methyl-4-hydroxy-4'-methyldiphenylamine in 10 ml of concentrated sulfuric acid at room temperature for 17 hours. The reaction production was poured into 100 ml of ice-cold water and the aqueous system was adjusted to pH9 with 20% aqueous solution of sodium hydroxide at room temperature to precipitate a solid. The solid was separated by filtration, washed with water, dried and then recrystallized from benzene to obtain 3-N-methyl-N-cyclopentylamino-6-methyl-7-p-toluidinofluoran as a colorless crystal in a 75% yield. The fluoran derivative had a melting point of 182°–185° C. and became black upon contact with silica gel.

EXAMPLE 5

Example 4 was repeated except that 2-(2-hydroxy-4-N-methyl-N-cycloheptylamino)benzoylbenzoic acid was instead of 2-(2-hydroxy-4-N-methyl-N-cyclopentylamino)benzoylbenzoic acid to obtain 3-N-methyl-N-cycloheptylamino-6-methyl-7-p-toluidinofluoran as a colorless crystal in a 73% yield. The fluoran derivative had a melting point of 173°–176° C. and became black upon contact with silica gel.

EXAMPLE 6

Example 4 was repeated except that 2-(2-hydroxy-4-N-methyl-N-3',3',5'-trimethylcyclohexylamino)benzoylbenzoic acid was used instead of 2-(2-hydroxy-4-N-methyl-N-cyclopentylamino)benzoylbenzoic acid to obtain 3-N-methyl-N-3',3',5'-trimethylcyclohexylamino-6-methyl-7-p-toluidinofluoran as a colorless crystal in a 70% yield. The fluoran derivative had a melting point of 178°–183° C. and became black upon contact with silica gel.

EXAMPLE 7

0.01 mol of 2-(2-hydroxy-4-N-n-octyl-N-cyclopentylamino)benzoylbenzoic acid and 0.01 mol of 2-methyl-4-ethoxydiphenylamine were reacted in 10 ml of concentrated sulfuric acid at room temperature for 24 hours. The reaction product was poured into 100 ml of ice-cold water and the aqueous system was adjusted to pH 11 with 20% aqueous solution of sodium hydroxide at room temperature. Further 30 ml of acetone was added to the aqueous system and then the mixture was refluxed for 3 hours. After removing acetone, produced crystalline precipitates were separated by filtration, washed with water and recrystallized from isopropylalcohol to obtain 3-N-n-octyl-N-cyclopentylamino-6-methyl-7-anilinofluoran as a colorless needles in a 71% yield. The fluoran derivative had a melting point of 165°–168° C. and became black upon contact with silica gel.

EXAMPLE 8

Example 7 was repeated except that 2-(2-hydroxy-4-N-methyl-N-4'-methylcyclohexylamino)benzoyl benzoic acid was used instead of 2-(2-hydroxy-4-N-n-octyl-N-cyclopentylamino)benzoylbenzoic acid to obtain 3-N-methyl-N-4'-methylcyclohexylamino-6-methyl-7-anilinofluoran as a colorless in a 80% yield. The fluoran derivative had a melting point of 250°–251° C. and became black upon contact with silica gel.

EXAMPLE 9

Example 7 was repeated except that 2-(2-hydroxy-4-N-ethyl-N-4'-t-butylcyclohexylamino)benzoylbenzoic acid was used instead of 2-(2-hydroxy-4-N-n-octyl-N-cyclopentylamino)benzoylbenzoic acid to obtain and ethylalcohol was used as a recrystallizing solvent to obtain 3-N-ethyl-N-4'-t-butylcyclohexylamino-6-methyl-7-anilinofluoran as colorless needles in a 81% yield. The fluoran derivative had a melting point of 256°–257° C. and became black upon contact with silica gel.

EXAMPLE 10

Example 9 was repeated except that 2-(2-hydroxy-4-N-methyl-N-4'-t-butylcyclohexylamino)benzoylbenzoic acid was used instead of 2-(2-hydroxy-4-N-ethyl-N-4'-t-butylcyclohexylamino)benzoylbenzoic acid to obtain 3-N-methyl-N-4'-t-butylcyclohexylamino-6-methyl-7-anilinofluoran as a colorless needles in a 84% yield. The fluoran derivative had a melting point of 205°–206° C. and became black upon contact with silica gel.

EXAMPLES 11 TO 53

Fluoran derivatives were prepared in the same manner as in Example 1 except that benzophenone derivatives described in Table 1 were used instead of 2-(2-hydroxy-4-N-methyl-N-cyclopentylamino)benzoylbenzoic acid and that p-aminophenol derivatives described in Table 1 were used instead of 2-methyl-4-methoxydiphenylamine. The yield of the fluoran derivatives and the color produced by contacting them with silica gel are shown in Table 1.

TABLE 1

| No | R | $R_1$ | X | Y | $R_2$ | $R_3$ | $R_6$ | Yield (%) | Color |
|----|---|-------|---|---|-------|-------|-------|-----------|-------|
| 11 | cyclopentyl | n-butyl | H | methyl | H | phenyl | methyl | 81 | black |
| 12 | cyclopentyl | isopentyl | " | ethyl | " | " | " | 83 | " |
| 13 | cyclopentyl | methyl | " | methyl | " | 2',4',6'-trimethylphenyl | " | 80 | " |
| 14 | cyclopentyl | " | " | " | " | p-n-butylphenyl | " | 85 | " |
| 15 | cyclopentyl | " | " | " | " | p-dimethylaminophenyl | " | 80 | " |
| 16 | cyclopentyl | " | " | H | " | m-trifluoromethylphenyl | " | 75 | " |
| 17 | cyclopentyl | " | " | " | " | o-chlorophenyl | " | 70 | " |
| 18 | cyclopentyl | " | " | " | " | o-methoxycarbonylphenyl | " | 61 | " |
| 19 | cyclopentyl | ethyl | " | chloro | methyl | n-octyl | " | 67 | reddish black |
| 20 | cyclopentyl | " | " | " | H | cyclohexyl | " | 63 | reddish black |
| 21 | cyclopentyl | " | " | methoxy | benzyl | phenyl | " | 31 | reddish black |
| 22 | cyclopentyl | benzyl | chloro | H | H | H | " | 45 | reddish black |
| 23 | cyclopentyl | ethyl | methyl | " | " | p-acetylphenyl | " | 45 | black |
| 24 | cyclopentyl | " | t-butyl | " | " | o-benzoylphenyl | " | 49 | " |
| 25 | cyclohexylmethyl | methyl | H | methyl | H | phenyl | methyl | 88 | black |
| 26 | cyclohexylmethyl | n-butyl | " | ethyl | " | " | ethyl | 84 | " |
| 27 | cyclohexylmethyl | isopentyl | " | methyl | " | " | methyl | 84 | " |
| 28 | cyclohexylmethyl | methyl | " | " | " | p-n-butylphenyl | " | 87 | " |
| 29 | cyclohexylmethyl | " | " | " | " | p-dimethylaminophenyl | " | 85 | " |
| 30 | cyclohexylmethyl | " | t-butyl | H | " | o-chlorophenyl | " | 61 | " |
| 31 | 4'-methylcyclohexyl | ethyl | H | " | methyl | m-trifluoromethylphenyl | " | 80 | greenish black |
| 32 | 4'-methylcyclohexyl | n-octyl | " | " | H | o-methoxycarbonylphenyl | " | 81 | black |
| 33 | 3'-methylcyclohexyl | methyl | " | methyl | " | phenyl | " | 81 | " |
| 34 | 2'-methylcyclohexyl | " | " | chloro | " | H | " | 67 | reddish black |
| 35 | 2'-methylcyclohexyl | " | " | methyl | " | phenyl | " | 85 | black |
| 36 | 2'-methylcyclohexyl | benzyl | " | H | " | n-octyl | " | 65 | greenish black |

TABLE 1-continued

| No | R | R₁ | X | Y | R₂ | R₃ | R₆ | Yield (%) | Color |
|----|---|-----|---|---|-----|-----|-----|-----|-------|
| 37 | cycloheptyl | ethyl | " | methoxy | " | phenyl | " | 69 | black |
| 38 | 3',3',5'-trimethylcyclohexyl | n-butyl | " | methyl | " | " | " | 80 | " |
| 39 | 3',3',5'-trimethylcyclohexyl | isopentyl | " | " | " | " | " | 75 | " |
| 40 | 3',3',5'-trimethylcyclohexyl | n-octyl | H | methyl | H | phenyl | methyl | 69 | black |
| 41 | 3',3',5'-trimethylcyclohexyl | ethyl | " | " | " | p-n-butylphenyl | " | 81 | " |
| 42 | 3',3',5'-trimethylcyclohexyl | " | " | " | " | p-dimethylaminophenyl | " | 72 | " |
| 43 | 3',3',5'-trimethylcyclohexyl | " | " | H | " | o-chlorophenyl | " | 79 | " |
| 44 | 3',3',5'-trimethylcyclohexyl | " | " | chloro | " | phenyl | " | 75 | " |
| 45 | 3',3',5'-trimethylcyclohexyl | " | " | H | " | m-trifluoromethylphenyl | " | 79 | reddish black |
| 46 | 3',3',5'-trimethylcyclohexyl | " | " | " | methyl | m-trifluoromethylphenyl | " | 81 | black |
| 47 | 3',3',5'-trimethylcyclohexyl | n-butyl | " | " | H | m-trifluoromethylphenyl | " | 71 | reddish black |
| 48 | 3',3',5'-trimethylcyclohexyl | isopentyl | " | " | " | m-trifluoromethylphenyl | " | 68 | reddish |
| 49 | 3',3',5'-trimethylcyclohexyl | benzyl | " | " | " | n-octyl | " | 58 | greenish black |
| 50 | 2',3'-dimethylcyclohexyl | methyl | " | methyl | " | phenyl | " | 78 | black |
| 51 | 2',3'-dimethylcyclohexyl | ethyl | " | " | " | " | " | 83 | " |
| 52 | 2',3'-dimethylcyclohexyl | n-butyl | " | " | " | p-tolyl | " | 80 | " |
| 53 | 2',3'-dimethylcyclohexyl | n-hexyl | " | " | " | " | " | 76 | " |

EXAMPLE 54

A heat-sensitive record material was prepared by the following method with the use of 3-N-ethyl-N-cyclopentylamino-6-methyl-7-anilinofluoran obtained in Example 1.

(1) Preparation of A liquid:

The following composition was passed through a sand mill.

| | |
|---|---|
| fluoran derivative obtained in Example 1 | 5 parts |
| stearic acid amide | 1 part |
| 2% aqueous solution of hydroxyethylcellulose | 25 parts |

Pulverization was continued until an average particle size of 2 microns.

(2) Preparation of B liquid:

The following composition was passed through a sand mill.

| | |
|---|---|
| 4,4'-isopropylidenediphenol | 50 parts |
| stearic acid amide | 10 parts |
| 2% aqueous solution of hydroxyethylcellulose | 250 parts |

Pulverization was continued until an average particle size of 2 microns.

(3) Making a heat-sensitive record material:

The following composition was mixed to prepare a coating composition.

| | |
|---|---|
| A liquid | 62 parts |
| B liquid | 31 parts |
| ultrafinely divided particles of silicic anhydride ("Syloid 244" manufactured by Fuji-Davidson Chemical) | 25 parts |
| 20% aqueous solution of a salt of styrene-maleic anhydride copolymer | 175 parts |
| zinc stearate | 5 parts |
| water | 100 parts |

The coating composition was coated on a base sheet of 50 g/m² in the weight of an amount of 6 g/m² on dry basis to obtain a heat-sensitive record material.

The obtained record material which had a good white paper like appearance without fogging, was pressed with a pressure of 4 kg/cm² for 5 seconds on a plate heated at 125° C. to develop deep black images. The color images were superior in light resistance. The color change and discoloration when exposed to sunlight were not substantially appreciated.

Images were recorded on the record material with the use of a cylindrical scanning recording machine at a scanning speed of 0.7 m/sec with $CO_2$ gas laser (output: 1 W, beam diameter: 150 microns). Resultantly, deep black images were obtained.

EXAMPLE 55

A heat-sensitive record material was prepared in the same manner as in Example 54 except that 3-N-ethyl-N-cyclohexylmethylamino-6-methyl-7-anilinofluoran obtained in Example 2 was used instead of 3-N-ethyl-N-cyclopentylamino-6-methyl-7-anilinofluoran.

The obtained record material which had a good white paper-like appearance without fogging, was pressed with a pressure of 4 kg/cm² for 5 seconds on a plate heated at 125° C. to develop deep black images. The color images were superior in light resistance. The color change and discoloration when exposed to sunlight were not substantially appreciated.

Images were recorded on the record material with the use of a cylindrical scanning recording machine at a scanning speed of 0.7 m/sec with $CO_2$ gas laser (output: 1 W, beam diameter: 150 microns). Resultantly, deep black images were obtained.

EXAMPLE 56

A heat-sensitive record material was prepared in the same manner as in Example 54 except that 3-N-ethyl-N-3′,3′,5′-trimethylcyclohexylamino-6-methyl-7-anilinofluoran obtained in Example 3 was used instead of 3-N-ethyl-N-cyclopentylamino-6-methyl-7-anilinofluoran.

The obtained record material which had a good white paper-like appearance without fogging, was pressed with a pressure of 4 kg/cm² for 5 seconds on a plate heated at 125° C. to develop black images. The color images were superior in light resistance. The color change and discoloration when exposed to sunlight were not substantially appreciated.

Images were recorded on the record material with the use of a cylindrical scanning recording machine at a scanning speed of 0.7 m/sec with $CO_2$ gas laser (output: 1 W, beam diameter: 150 microns). Resultantly, deep black images were obtained.

EXAMPLE 57

5 parts of fluoran derivative obtained in Example 1 was dissolved in 100 parts of isopropylated naphthalene. The resultant solution was dispersed in 350 parts of warm water (50° C.) containing 25 parts of pigskin-gelatin having an isoelectric point of 8 and 25 parts of gum arabic dissolved in it to obtain an emulsion. 1000 parts of warm water was added to the emulsion. The mixture was adjusted to pH 4 with acetic acid and cooled at 10° C. 10 parts of 25% aqueous solution of glutaraldehyde was added to it to solidify capsules. The capsule-containing coating composition was coated on one surface of a base sheet of 45 g/m² in the weight of 5 g/m² on dry basis and an acceptor coating composition comprising 20 parts of zinc 3,5-di-(α-methylbenzyl)salicylate, 80 parts of kaolin and 30 parts of styrene-butadiene copolymer emulsion (solid content: 50%) dispersed in 200 parts of water was coated on another surface of the base sheet in the weight of 5 g/m² on dry basis to obtain a pressure-sensitive record material (middle sheet).

Several of the pressure-sensitive record material were piled in the manner as the capsule coated layer was closed to the acceptor coated layer, pressed with driving a pen to obtain black color images on the acceptor coated surface. The color images were obtained with a rapid color development and in a deep color immediately after press, and the color change and discoloration were not appreciated when exposed to sunlight.

EXAMPLE 58

A pressure-sensitive record material was prepared in the same manner as in Example 57 except that fluoran derivative obtained in Example 2 was used instead of fluoran derivative obtained in Example 1.

Several of the pressure-sensitive record material were piled in the manner as the capsule coated layer was closed to the acceptor coated layer, pressed with driving a pen to obtain black color images on the acceptor coated surface. The color images were obtained with a rapid color development and in a deep color immediately after press, and the color change and discoloration were not appreciated when exposed to sunlight.

EXAMPLE 59

A pressure-sensitive record material was prepared in the same manner as in Example 57 except that fluoran derivative obtained in Example 3 was used instead of fluoran derivative obtained in Example 1.

Several of the pressure-sensitive record material were piled in the manner as the capsule coated layer was closed to the acceptor coated layer, pressed with driving a pen to obtain black color images on the acceptor coated surface. The color images were obtained with a rapid color development and in a deep color immediately after press, and the color change and discoloration were not appreciated when exposed to sunlight.

EXAMPLE 60

200 parts of cuprous iodide and 5 parts of 10% aqueous solution of sodium sulfite were added to 200 parts of 1% aqueous solution of polyvinyl alcohol. The mixture was passed through a sand mill. Pulverization was continued until an average particle size of 2 microns. To the pulverized mixture 8 parts of polyacrylate emulsion and 20 parts of titanium dioxide were added and thoroughly dispersed. The dispersion was coated on a base sheet of 50 g/m² in the weight of 7 g/m² on dry basis. Further, there was coated on the coating layer in the weight of 5 g/m² on dry basis a heat-sensitive coating composition prepared by the same manner as in Example 54 except that 3-N-methyl-N-cyclopentylamino-6-methyl-7-p-toluidinofluoran obtained in Example 4 was used instead of 3-N-ethyl-N-cyclopentylamino-6-methyl-7-anilinofluoran to obtain an electrothermal record material.

Images were recorded on the record material with the use of a cylindrical scanning recording machine at a scanning speed of 630 mm/sec with a needle pressure of 10 g. The record images were deep black. The color images were superior in light resistance. The color change and discoloration when exposed to sunlight were not substantially appreciated.

EXAMPLE 61

An electrothermal record material was prepared in the same manner as in Example 60 except that 3-N-methyl-N-4'-methylcyclohexylamino-6-methyl-7-anilinofluoran obtained in Example 8 was used instead of 3-N-methyl-N-cyclopentylamino-6-methyl-7-p-toluidinofluoran.

Images were recorded on the record material with the use of a cylindrical scanning recording machine at a scanning speed of 630 mm/sec with a needle pressure of 10 g. The record images were deep black. The color images were superior in light resistance. The color change and discoloration when exposed to sunlight were not substantially appreciated.

EXAMPLE 62

An electrothermal record material was prepared in the same manner as in Example 60 except that 3-N-ethyl-N-4'-t-butylcyclohexylamino-6-methyl-7-anilinofluoran obtained in Example 9 was used instead of 3-N-methyl-N-cyclopentylamino-6-methyl-7-p-toluidinofluoran.

Images were recorded on the record material with the use of a cylindrical scanning recording machine at a scanning speed of 630 mm/sec with a needle pressure of 10 g. The record images were deep black. The color images were superior in light resistance. The color change and discoloration when exposed to sunlight were not substantially appreciated.

What we claim is:

1. A fluoran derivative, as a new article of a compound, having the following formula:

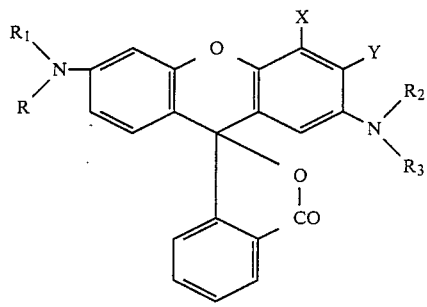

wherein R is cyclopentyl, cycloheptyl, cyclohexylmethyl or cyclohexyl substituted by at least one alkyl and having 7 to 10 carbon atoms; $R_1$ is an alkyl having 1 to 8 carbon atoms, $R_2$ is hydrogen, $R_3$ is a phenyl which may be substituted by at least one substituent selected from the group consisting of alkyls having 1 to 4 carbon atoms, halogen atoms and halogen substituted methyls, X is hydrogen and Y is hydrogen or an alkyl having 1 to 4 carbon atoms.

2. A fluoran derivative as defined in claim 1, wherein Y is an alkyl having 1 to 4 carbon atoms.
3. A fluoran derivative as defined in claim 1, wherein R is cyclopentyl.
4. A fluoran derivative as defined in claim 1, wherein R is cycloheptyl, cyclohexlmethyl or methyl cyclohexyl.
5. A fluoran derivative as defined in claim 1, wherein R is dimethylcylohexyl, trimethylcyclohexyl or t-butylcyclohexyl.
6. A recording system which utilizes a color forming reaction between a colorless chromogenic material and an electron accepting acidic reactant material, characterized in that said colorless chromogenic material comprises at least one fluoran derivative having the following formula:

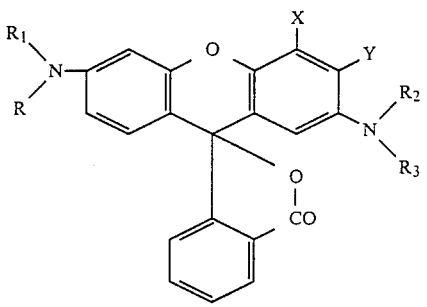

wherein R is cyclopentyl, cycloheptyl, cyclohexylmethyl or cyclohexyl substituted by at least one alkyl and having 7 to 10 carbon atoms; $R_1$ is an alkyl having 1 to 8 carbon atoms, $R_2$ is hydrogen, $R_3$ is a phenyl which may be substituted by at least one substituent selected from the group consisting of alkyls having 1 to 4 carbon atoms, halogen atoms and halogen substituted methyls, X is hydrogen and Y is hydrogen or an alkyl having 1 to 4 carbon atoms.

7. A recording system according to claim 6, in which said recording system is a pressure-sensitive recording system.
8. A recording system according to claim 6, in which said recording system is a heat-sensitive recording system.

* * * * *